United States Patent [19]

Mageli et al.

[11] 4,129,700
[45] Dec. 12, 1978

[54] PEROXY COMPOUNDS AND VULCANIZABLE COMPOSITIONS THEREOF

[75] Inventors: Orville L. Mageli, Kenmore, N.Y.; William A. Swarts, Dover, N.J.

[73] Assignee: Pennwalt Corporation, Philadelphia, Pa.

[21] Appl. No.: 596,778

[22] Filed: Jul. 17, 1975

[51] Int. Cl.² .................................................. C08F 8/30
[52] U.S. Cl. ............................. 260/823; 260/453 R; 260/453 RZ; 260/463; 526/57; 560/33; 560/115; 560/24; 260/773; 560/167; 568/558
[58] Field of Search ............... 526/49, 57; 260/453 R, 260/453 RZ, 463, 482 C, 471 C, 468 E; 560/166

[56] References Cited
U.S. PATENT DOCUMENTS

| 3,225,079 | 12/1965 | Harrison et al. | 260/463 |
| 3,236,872 | 2/1966 | Manley et al. | 526/57 |
| 3,264,274 | 8/1966 | Leveskis | 260/453 RZ |
| 3,671,651 | 6/1972 | D'Angelo | 260/463 |
| 3,706,818 | 12/1972 | Mageli et al. | 260/482 C UX |
| 3,725,455 | 4/1973 | D'Angelo et al. | 526/57 X |
| 3,839,390 | 10/1974 | D'Angelo et al. | 260/453 RZ X |
| 3,879,353 | 4/1975 | Crawford | 260/453 RZ X |

Primary Examiner—William F. Hamrock

[57] ABSTRACT

A novel class of compounds having the formula

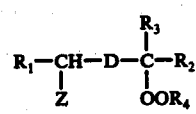

where Z is a substituted carbonate or carbamate, D is an alkynyl or an alkyl, and the R's may be alkyl.

8 Claims, No Drawings

PEROXY COMPOUNDS AND VULCANIZABLE COMPOSITIONS THEREOF

BACKGROUND OF THE INVENTION

1. Field of the invention

This invention relates to novel compounds having both a peroxy group and a substituted hydroxy group attached to a backbone chain of at least 4 carbons. These novel compounds are especially useful as agents for the crosslinking or vulcanizing polymers. This invention also relates to vulcanizable compounds of these novel compounds and to an improved method of making a crosslinked or vulcanized material using the novel peroxy compounds as a crosslinking agent.

2. Description of the prior art

U.S. Pat. No. 3,236,872 (Manly et al) discloses hexylene glycol hydroperoxides and certain alkyl and ester derivatives thereof having the formula

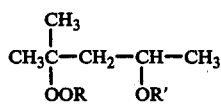

where R and R' are hydrogen, acyl, aroyl or alkyl groups. These compounds are also disclosed as crosslinking agents. Manly et al is completely silent on the preparation of carbonate or carbamate derivatives of the so-called hexylene glycol peroxides shown by the formula supra.

SUMMARY OF THE INVENTION

The novel class of peroxides of this invention have the following general structure:

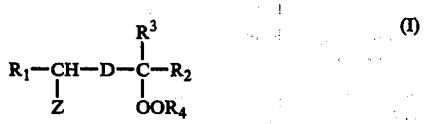

where:

(a) $R_1$ is hydrogen or an alkyl of 1–4 carbons;

(b) $R_2$ and $R_3$ are independently an alkyl of 1 to 8 carbons;

(c) $R_4$ is t-alkyl of 4–10 carbons, t-aralkyl of 9–16 carbons,

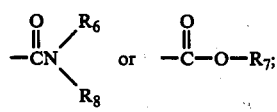

(d) Z is

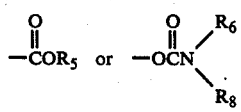

(e) $R_5$ and $R_7$ are independently an alkyl of 1–8 carbons, a cycloalkyl of 5 to 11 carbons, an aralkyl of 7–18 carbons or an aryl having one or more benzene nuclei which may be fused or condensed.

(f) $R_6$ and $R_8$ are independently hydrogen, alkyl of 1–8 carbons, cycloalkyl of 5 or 6 carbons, phenyl or alkylphenyl of 7–10 carbons; and (g) D is an alkynyl diradical or alkyl diradical having 1–8 carbons.

DETAILED DESCRIPTION OF THE INVENTION

It has been discovered that certain new derivatives of 1,3-dimethyl-3-hydroperoxybutyl alcohol (hexylene glycol hydroperoxide) or 1,3-dimethyl-3-(t-butylperoxy)butyl alcohol (hexylene glycol t-butyl peroxide), namely the carbonate or carbamate derivatives, have specially efficacious properties as crosslinking or vulcanizing agents when compared to the prior art compounds. In other words, Applicants have surprisingly found that their carbonate and carbamate derivatives have a better crosslinking efficiency than the prior art compounds; the carbonate and carbamate derivatives give crosslinking efficiencies of 85% or better at 10 milliequivalents for 100 parts of polymeric compound whereas the carboxylate derivatives covered in the prior art give in general polyethylene (PE) crosslinking efficiencies at or below 80%.

COMPOUNDS I

In the compound

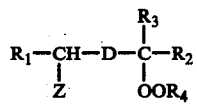

the backbone structure

has at least 4 carbons; the backbone may have up to 22 carbons but commonly has 5–18 carbons. At least one carbon separates the tertiary carbon

to which the peroxy group is joined from the carbon

to which the carbonate or carbamate radical is joined. D is an alkynyl diradical of 2–8 carbons or an alkyl diradical of 1–8 carbons which may be straight or branched chain.

$R_1$ is either a hydrogen or an alkyl of 1–4 carbons such as methyl, propyl or butyl.

$R_2$ and $R_3$ are independently an alkyl of 1 to 8 carbons, but preferably of 1 to 4 carbons such as methyl, ethyl or butyl group.

$R_4$ is a tertiary alkyl radical of 4–10 carbons with a preferred range of 4–8 carbons. $R_4$ may be tertiary aralkyl of 9–15 carbons or tertiary cycloalkyl of 6–10 carbons. $R_4$ may also be

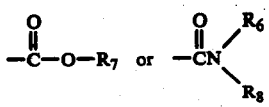

where $R_7$ is an alkyl of 1–8 carbons, a cycloalkyl of 5–11 carbons, an aralkyl of 7–18 carbons or an aryl having one or more benzene nuclei which may be fused or condensed. $R_6$ and $R_8$ are independently hydrogen, alkyl of 1–8 carbons, cycloalkyl of 5 or 6 carbons, phenyl or alkylphenyl of 7–10 carbons.

Z is either

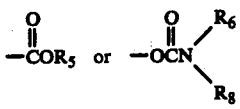

where $R_5$ has the same definition as $R_7$ but is independent thereof. $R_6$ and $R_8$ have been defined supra.

Typical peroxy compounds of the invention are:
1. 1,3-Dimethyl-3-(ethoxycarbonylperoxy)butyl ethyl carbonate.
2. 1,3-Dimethyl-3-(t-butylperoxy)butyl n-butyl carbonate.
3. 1,3-Dimethyl-3-(t-butylperoxy)butyl N,N-dimethylcarbamate.
4. 1,3,Dimethyl-3-(t-butylperoxy)butyl N-methylcarbamate.
5. 1,3-Dimethyl-3-(t-butylperoxy)butyl carbamate.
6. 1,3-Dimethyl-3-(N-cyclohexylcarbamoylperoxy)butyl N-cyclohexylcarbamate.
7. 1,3-Dimethyl-3-(N,N-dimethylcarbamoylperoxy)butyl N,N-dimethylcarbamate.
8. 4-Methyl-4-(t-butylperoxy)pentyl N,N-dimethylcarbamate.
9. 4-Methyl-4-(isoproxycarbonylperoxy)pentyl isopropyl carbonate.
10. 1,4-Dimethyl-4-(t-butylperoxy)pentyl isopropyl carbonate.
11. 1,3,3,5-Tetramethyl-5-(N,N-dimethylcarbamoylperoxy)-hexyl N,N-dimethylcarbamate.
12. 1-(Ethoxycarbonyloxy)-4-(t-butylperoxy)-4-methyl-pent-2-yne, otherwise named 4-Methyl-4-(t-butylperoxy)-pent-2-ynyl ethyl carbonate.
13. 1-(N,N-dimethylcarbamoyloxy)-4-(N,N-dimethylcarbamoyl-peroxy)-4-methyl-pent-2-yne, otherwise named 4-methyl-4-(N,N-dimethylcarbamoylperoxy)-pent-2-ynyl N,N-dimethylcarbamate.
14. 3,7-Dimethyl-7-(t-butylperoxy)octyl N,N-dimethylcarbamate.
15. 3,7-Dimethyl-7-(t-butylperoxy)octyl n-butyl carbonate.
16. 2-[N-(4-Methylphenyl)carbamoyloxy]-4-n-butyl-4-(α,α-dimethylbenzylperoxy)octane.
17. 2-(2-Ethylhexoxycarbonyloxy)-7-methyl-7-(α,α-dimethyl-4-phenylbenzylperoxy)octa-3,5-diyne.
18. 1-(N,N-Di-n-butylcarbamoyloxy)-9-methyl-9-(2-pinanylperoxy)-decane.
19. 2-(N-Cyclopentylcarbamoyloxy)-4-methyl-4-(1,1,3,3-tetramethylbutylperoxy)pentane.

In general, the compounds I are prepared by the reaction of a glycol (or diol) with a hydroperoxide to form an intermediate that can then be converted into the compounds of the invention by the methods described in the Examples hereinafter. The glycol may be a primary-tertiary or a secondary-tertiary compound. Examples of the glycol are:
(1) Hexylene glycol(1,3-dimethyl-3-hydroxybutyl alcohol),
(2) 3,7-Dimethyl-7-hydroxyoctyl alcohol,
(3) 4-Methyl-4-hydroxypentyl alcohol,
(4) 1,4-Dimethyl-4-hydroxypentyl alcohol,
(5) 1,3,3,5-Tetramethyl-5-hydroxyhexyl alcohol,
(6) 4-Methyl-4-hydroxypent-2-ynyl alcohol,
(7) 2,4-dihydroxy-2-methyloctane,
(8) 2,4-dihydroxy-4-methyloctane,
(9) 2,4-dihydroxy-4-n-butyloctane,
(10) 9-hydroxy-9-methyldecanol, and
(11) 2,7-dihydroxy-2-methylocta-3,5-diyne.

The hydroperoxide reactant may be t-alkyl, t-aralkyl, t-cycloalkyl, or t-alkynyl. Examples of this reactant are the t-butyl, t-amyl, 1,1,3,3-tetramethylbutyl, α-cumyl, β-isopropl-α-cumyl, β-menthyl, pinanyl, 1-methyl-cyclohexyl, or the 1,1-dimethylprop-2-ynyl hydroperoxide.

Compounds I are useful as initiators for vinyl polymerization, flame retardant synergists for polystyrene, free radical catalysts, and intermediates in organic synthesis. These compounds are effective crosslinking agents for polymers and especially effective for polyolefins and elastomers.

Compounds I can be positioned on a support carrier when the ultimate use makes such a composition desirable; for example, in rubber compounding, any solid which does not react with the peroxy compound may be used as a carrier. Suitable carriers are silicates, clays, talc, magnesium carbonate and carbon blacks. The silicates and magnesium carbonate are especially preferred carriers.

Compounds I are especially effective crosslinking (vulcanizing) agents for polymeric compounds which are capable of being crosslinked to form a thermoset material. The compound should be intimately mixed with the polymeric compound in a sufficient amount to afford the desired degree of crosslinking. (Note that the words of art, "vulcanizing" and "crosslinking", are used as synonyms).

THE POLYMERIC COMPOUNDS

The polymeric compounds include any of those natural and synthetic materials which are thermoplastic or have indefinite melting points and which can be transformed to thermoset materials (elastic, or somewhat rigid solids) by a crosslinking reaction, especially through the action of an added agent. Examples are the polymeric compounds produced by the vulcanizing of natural and synthetic rubber by means of sulfur or peroxy compounds.

Polymeric compounds, that illustrate this invention, are as follows:
(1) Solid polyolefins wherein the preferred ones are polyethylene and polybutenes.
(2) Elastomers such as natural rubber.
(3) Synthetic rubbers such as butyl rubbers, styrene-butadiene (GR-S) rubber, neoprene, acrylic rubber, Buna rubber, ethylenepropylene rubber (copolymer and terpolymer), polyurethane rubbers, nitrile rubbers and the silicone rubbers.
(4) Vinyl polymers such as polyvinyl chloride (PVC), polyvinyl acetate (PVAC), PVC-PVAC copolymers, ethylene-vinyl acetate copolymer and the vinyl pyrrolidone polymers and copolymers.

(5) Miscellaneous "elastomers" such as polybutene-styrene copolymers, ethylene and/or propylene-styrene copolymers and acrylonitrile-butadiene-styrene (ABS) copolymers.

(6) Various polyether resins, polyester resins, polyamide resins and natural gums.

The solid polyolefins and elastomers are especially suitable polymeric compounds. The polymers may include plasticizers and/or oil extenders.

VULCANIZABLE COMPOUNDS

It has been discovered that an intimate mixture of the defined polymer and the defined peroxy agent can be heat-cured in reasonable times at reasonable temperatures to a crosslinked (vulcanized) material. The temperature and time are controlled to obtain the desired degree of crosslinking. Sufficient agent is present to afford the desired degree of crosslinking.

The peroxy compounds of the invention can be used alone or in conjunction with a coagent or coupling agent — just as the presently known vulcanizing agents are used. Suitable coagents are: sulfur, viscous polybutadiene resins such as Enjay Buton 150, ethylene dimethacrylate, maleic acid, vinyl silane, N,4-dinitroso-N-methyl aniline and hexachlorocyclopentadiene.

In addition to the defined polymeric compound and defined peroxy compound in intimate mixture, the vulcanizable composition may include coagents, promoters, coupling agents, fillers, reinforcing materials, and any other material conventionally used in the production of vulcanized compositions. Desirable fillers are carbon black, titanium dioxide, calcium silicate and the alkaline earth metal carbonates. A preferred filler is the alkaline carbon blacks.

Examples of the novel mix (as parts by weight per 100 parts by weight of polymeric compound) are:

MIXTURE A includes
(a) 100 parts by weight of EPR (an ethylene-propylene copolymer),
(b) 1-5 PHR of a peroxy compound of the invention,
(c) 0.1-0.5 parts of a coagent such as sulfur, and
(d) 50-60 parts carbon black.

MIXTURE B includes
(a) low density polyethylene and
(b) about 1-5 PHR of a peroxy compound of the invention.

MIXTURE C includes
(a) low density polyethylene,
(b) about 40-50 PHR of carbon black filler, and
(c) about 1-5 PHR of a peroxy compound of the invention.

MIXTURE D (a polyurethane rubber mixture) includes
(a) 100 parts of Genthane-S-polyurethane rubber,
(b) 25 PHR of carbon black, and
(c) 1-5 PHR of a peroxy compound of the invention.

It must be noted that oil extended EPR can be used in formulations; such a blend consists of 100 parts by weight of EPR and 40 parts by weight of mineral oil. This blend has a specific gravity of 0.86, a Mooney viscosity (8mL/212° F) of 40 and an ash content of 0.6 weight percent.

The vulcanizable composition has the solid polymeric compound, crosslinking agent and other materials in the formulation present in the form of an intimate mixture. The formulation components are milled together until a suitable mixture has been obtained. Elevated temperatures may be used to assist in the mixing.

The mixing temperatures and time should be controlled wth these defined peroxy compounds in order to avoid premature curing or localized curing. In the case of elastomers, for example, the Banbury mixers may reach a working temperature of 250°-260° F. Hence, the vulcanizable composition should have a cure time at these temperatures which permits good mixing without the premature cure, known as scorching in the rubber industry.

The defined peroxy compounds are present in the vulcanizable compositions of the invention in an amount sufficient to afford the desired degree of crosslinking. The amount needed is dependent on the type of polymeric compound present and the types and amounts of coagent and promoters present. In general 0.01 gram-equivalent of a peroxide will cure 100 grams of EPR (for a monofunctional peroxide the equivalent weight is equal to the molecular weight). Different end uses, however, will require more or less crosslinks (frequently an excess of 25 to 100% is used).

In industry the terminology PHR (parts per hundred parts of polymer or resin) is commonly used in stating formulations. The peroxy compounds of this invention are generally present in a vulcanizable composition in an amount comprising about 1-5 PHR.

VULCANIZED COMPOSITIONS

The vulcanizable composition is heat cured for a time sufficient to obtain the desired degree of crosslinking. The heat curing has a temperature-time relationship which is primarily dependent on the polymeric compound and the peroxy agent present; the heat curing is also affected by the formulation as a whole. It is customary to use a time equal to about 6-8 half-lives of the peroxy agent.

In the case of elastomers, the vulcanizing may be carried out at a temperature of about 270°-600° F. The cure time is inversely related to temperature. The curing temperature can range from about 270° to 400° F and the curing time can vary from about 1 minute to 240 minutes (4 hours). At the higher temperatures the shorter times are used keeping in mind that the heating cycle for each particular peroxide should be such that the peroxide undergoes a time-temperature profile of 6 to 8 half-lives. The defined peroxy agents give acceptable cure times at the lower temperatures; this is advantageous to producers because lower temperatures reduce the possibility of "burning" and the shorter times permit a greater output in a given piece of equipment. In the case of polyolefin and elastomer formulations, the preferred peroxy agents heat cure at a temperature-time relationship of about 300°-340° F and about 10-30 minutes (the longer times are associated with the lower temperatures). Using somewhat longer times wthout significant change in the quality of the product has been observed.

The heat cured (vulcanized) product may develop better physical properties on maturing at ordinary temperatures. In the case of elastomers such a period seems desirable; a 16-24 hour maturing period is sufficient.

The heat curing may be carried out in any of the manners now used in the polymer compounding and rubber compounding art. These may be mold cures, oil cures where oil does not harm the polymeric compound, oven cures, steam cures or hot metal bath cures.

EXAMPLES

PREPARATION OF THE COMPOUNDS OF THE INVENTION

EXAMPLE I 1,3-Dimethyl-3-(t-butylperoxy)butyl n-butyl carbonate (C-I)

To a solution of 8.1 g. (0.11 mole) of n-butyl alcohol and 7.9 g. (0.1 mole) of pyridine in diethyl ether cooled to 10°±1° C was added a solution of 27.0 g. (0.1 mole) 1,3-dimethyl-3-(t-butylperoxy)butyl chloroformate. The reaction temperature was controlled at 15°±1° C during the addition.

After the addition was complete the reaction mixture was allowed to stir for 2 hours at 20°±1° C. The reaction mixture was then diluted with water and the organic phase was separated, washed with a 10% aqueous solution of tartaric acid and water to neutrality.

The organic phase was then dried over anhydrous magnesium sulfate, filtered and the solvent removed unde reduced pressure.

After further purification by column chromatography 24 g. of a viscous liquid was obtained. It was identified by means of Infrared spectroscopy.

EXAMPLE II 1,3-Dimethyl-3-(ethoxycarbonylperoxy)butyl ethyl carbonate (C-II)

To a solution of 24.4 g. (0.0786 mole) of (86.4%) 1,3-dimethyl-3(ethoxycarbonylperoxy)butyl chloroformate in 100 ml of diethyl ether, cooled at 10°±1° C was added a solution of 4.6 g (0.1 mole) of ethanol and 7.9 g. (0.1 mole) of pyridine in 25 ml of diethyl ether over a period of 20 minutes.

After the addition was completed the reaction mixture was allowed to stir for four hours while the reaction temperature was allowed to rise to 22°±1° C.

The pyridine hydrochloride was filtered off and the organic phase was washed with 10% solution of tartaric acid and water to neutrality, then dried over anhydrous magnesium sulfate, filtered and the solvent evaporated under reduced pressure. A liguid weighing 18.7 g. was recovered. The recovered product assayed 87.4% by active oxygen assay.

EXAMPLE III 1,3-Dimethyl-3-(t-butylperoxy)butyl N-methylcarbamate (C-III)

A solution of 105 g. (0.5 mole) 90% 1,3-Dimethyl-3-t-butylperoxy)butyl alcohol in 150 ml of cyclohexane was placed in a reactor equipped with a magnetic stirrer, a condenser protected by a calcium chloride drying tube and a thermometer. To the above was added 43 g. methyl isocyanate (50% excess — 28.5 g. (0.5 mole) theoretically needed).

An additional 50 ml of cyclohexane and a few crystals of Dabco* were then added. The reaction mixture was heated to 60° C over a period of about 1 hour and allowed to stir at this temperature for 4 hours. The reaction mixture was then allowed to cool to room temperature and stir overnight.

*Urethane Catalyst — Triethylene diamine — Houdry Process and Chem Co.

The reaction mixture was stripped of volatile material under vacuum and 100 ml of cyclohexane added to the residue. This solution was then washed with water to remove the Dabco catalyst, and also with a 40% aqueous ammonium sulfate solution. After drying over anhydrous sodium sulfate, the cyclohexane was removed under vacuum and a yield of 131.9 g. was obtained. The product was identified by infrared techniques.

EXAMPLE IV 1,3-Dimethyl-3-(t-butylperoxy)butyl N,N-dimethylcarbamate (C-IV)

To a solution of (97%) 1,3-dimethyl-3(t-butylperoxy)butyl chloroformate 5.2 g. (0.02 mole) in diethyl ether, cooled to 0°±1° C was added a solution of dimethylamine, 1.8 g. (0.04 mole) in diethyl ether over a period of 10 minutes. After the addition was complete the mixture was allowed to stir for two hours while the reaction temperature was allowed to rise to 20°±1° C. The reaction mixture was then filtered to remove the amine hydrochloride and the organic phase washed with 10% aqueous Tartaric acid solution and water to neutrality.

The ethereal phase was dried over magnesium sulfate, filtered and the solvent evaporated under vacuum. A yield of 5.1 grams of a colorless liquid was obtained which was identified by infrared spectroscopy.

EXAMPLE V 1,3-Dimethyl-3-(N-cyclohexyl-carbamoylperoxy)butyl N-cyclohexylcarbamate (C-V)

A mixture of 18.7 g. (0.15 mole) of cyclohexyl isocyanate, 6.7 g. (0.05 mole) of 1,3-dimethyl-3-hydroperoxybutyl alcohol and 3 drops of triethylamine was stirred for 5 days at ambient temperature. The reaction vessel was protected with a calcium chloride tube to keep out moisture. Within 2 days, a solid began to appear, and after the 5 day stirring period the reaction mixture was stripped in vacuo. The residue was slurried in 100 ml of ether and filtered. The filter cake was washed with an additional 30 ml of ether and air dried. A total of 7.5 grams of a colorless solid was obtained.

The solid was taken up in 150 ml of boiling ether and then filtered. The residue weighed 1.5 grams and melted at 224°–226° C and was identified as N,N'-dicyclohexlurea.

The ethereal filtrate was concentrated and cooled to 0° C and a colorless solid separated. A total of 4.6 g. of the desired product with a melting point of 115°–117° C, assaying 99% based on active oxygen content was obtained.

EXAMPLE VI 1,3-Dimethyl-3-(t-butylperoxy)butyl isopropyl carbonate (C-VI)

A four-necked 500 ml. round-bottomed flask was equipped with a mechanical stirrer, reflux condenser surmounted by calcium chloride drying tube, addition funnel and thermometer. A solution of 19 g. (0.1 mole) 1,3-dimethyl-3-(t-butylperoxy)butyl alcohol and 13.3 g (slightly over 0.1 mole) quinoline in 250 ml. pentane was placed in the flask which was placed in a water bath at 22½° C. Then 12.3 g (0.1 mole) isopropyl chloroformate was added dropwise over 5 minutes; the temperature did not rise over 23° C. Reaction was not complete after 3 days. Another 3 g. of quinoline was added, and the reaction was completed after another 3 days as indicated by the fact that no further precipitate of quinoline hydrochloride formed when an aliquot of clean pentane solution was withdrawn from the reaction mixture and allowed to stand for 15 minutes. The quinoline hydrochloride was filtered off and washed with 25 ml pentane which was added to the pentane solution. This solution was then successively washed with 25 ml. of 7% hydrochloric acid, two 50 ml. portions of water, and finally dried over sodium sulfate. After removal of drying agent and pentane, a yield of 23.8 g. (86.4%) of material found to be 1,3-dimethyl-3-(t-butylperoxy)butyl isopropyl carbonate by infrared analysis, was obtained.

etc., in the presence of a base (see Table A) at 0° C to about 50° C. After a 2 to 4 hour period of stirring, the resulting mixture was poured into water, additional organic solvent was added and the organic phase was separated from the aqueous phase. The organic phase was then washed with aqueous dilute mineral acid solution, then with aqueous base, and finally with water to neutral. After drying over anhydrous $MgSO_4$ the filtered solution was stripped of solvent in vacuo leaving the desired product.

Table A

Additional Derivatives of 1,3,-Dimethyl-3-(t-Butylperoxy)butyl Alcohol

| | Reactant[1] | Base | Product | Assay, % | Corr. Yield, % |
|---|---|---|---|---|---|
| VIII | $CH_2=CHCH_2NH_2$ | Sodium Carbonate | N-allyl O-[1,3-dimethyl-3-(t-butylperoxy)butyl] carbamate | — | 100 (uncorr.) |
| IX | $(CH_3)_3CNH_2$ | Triethylamine | N-t-butyl O-[1,3,dimethyl-3-(t-butylperoxy)butyl] carbamate | — | 99.0 (uncorr.) |
| X | $(CH_3)_3CCH_2C(CH_3)_2NH_2$ | Triethylamine | N-(1,1,3,3-tetramethylbutyl) O-[1,3-dimethyl-3-(t-butylperoxy)butyl]carbamate | — | 90.0 (uncorr.) |
| XI | 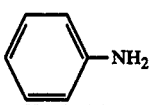 | Triethylamine | N-phenyl O-[1,3-dimethyl-3-(t-butylperoxy)butyl] carbamate | — | 48.5 (uncorr.) m.p. 57–61° C |
| XII | $C_2H_5C(CH_3)_2OH$ | Triethylamine | t-amyl 1,3-dimethyl-3-(t-butylperoxy)butyl carbonate | — | 87.0 (uncorr.) |

[1]Each of Reactants in Table A was reacted with 1,3-dimethyl-3-(t-butylperoxy)butyl chloroformate.

EXAMPLE VII 3,7-Dimethyl-7-(t-butylperoxy)octyl n-butyl carbonate (C-VII)

To a solution of 7.9 g (0.03 mole) of 3,7-dimethyl-7-(t-butylperoxy)octyl alcohol and 2.4 g (0.03 mole) of pyridine in diethyl ether cooled at 10°±1° C was added a solution of 4.09 (0.03 mole) of n-butyl chloroformate in diethyl ether. The reaction temperature was maintained at 15°±1° C during the addition.

The reaction mixture was allowed to react for 2 hours at 20°±1° C. The reaction mixture was diluted with water and the organic phase separated, washed with 10% aqueous solution of tartaric acid and water to neutrality.

The ethereal solution was dried over anhydrous magnesium sulfate, filtered and the solvent removed under reduced pressure.

A colorless liquid weighing 8g was obtained. It was identified by means of Infrared Spectroscopy.

The above-mentioned starting reactant, 3,7-dimethyl-7-(t-butylperoxy)octyl alcohol, was prepared by first reacting 3,7-dimethyl-7-hydroxy octyl alcohol with hydrogen peroxide to form 3,7-dimethyl-7-(hydroperoxy)octyl alcohol which was then alkylated with t-butyl alcohol to give said starting reactant.

EXAMPLES VIII to XII

Preparations of Additional 1,3-Dimethyl-3-(t-Butylperoxy)butyl Alcohol Derivatives Table A summarizes yields, assays and other synthetic data on several additional 1,3-dimethyl-3-(t-butylperoxy)butyl alcohol derivatives. The following general procedure was employed for their preparations:

One equivalent of 1,3-dimethyl-3-(t-butylperoxy)butyl chloroformate was slowly added to one equivalent of reactant (see Table A), dissolved in a solvent inert to the reaction such as pentane, benzene, diethyl ether, It is noted that certain of the prior art peroxide compounds, used as reactants in the Examples, are disclosed and prepared in U.S. Pat. No. 3,671,651 issued to O. L. Mageli and A. J. D'Angelo.

ILLUSTRATION

The following tables show comparative tests run on vulcanized compositions of the invention and prior art.

The components of the exemplary formulations, whether ethylene-propylene rubber (EPR), polyurethane rubber, or polyethylene, were milled to an intimate plastic mixture or a standard roll mill such as used in the rubber industry. The temperature of the mix during milling was held below 250° F. Under these conditions no scorching occurred in any embodiment.

The intimately mixed vulcanizable mass was removed from the roll mill and a portion placed in a mold and heat cured in a hydraulic press. The standard curing time was about 20–30 minutes at 320° F; other temperatures and times may be used too. Higher temperatures require shorter cure times.

Immediately upon removal from the curing press, the cured slabs are permitted to mature at room temperature for about 24 hours. This time was sufficient to give reproducible results from control compositions.

For EPR and polyurethane rubber formulations, the matured slabs were cut into dumbell shaped specimens and tested for tensile strength on an Instron Tensile Tester following ASTM procedure in D412-61T, "Tension Testing of Vulcanized Rubber".

For polyethylene formulations an inch square portion, about 1 gram in weight, was cut from the cured slab and used to determine the percent of crosslinking extracting the slab in xylene at 80° C for 24 hours. Note that other well known solvent extraction procedures could have been used. The percent of crosslinking, reported in Table II, represents the percent of insolubles not extracted from the slab.

TABLE I

CROSSLINKING EPR

| FORMULATION | INVENTION | PRIOR ART |
|---|---|---|
| EPR 404 (parts by weight) | 100 | 100 |
| SRF BLACK (PHR) | 60 | 60 |
| Sulfur (PHR) | .33 | .33 |
| 1,3-Dimethyl-3-(t-butylperoxy)butyl N-methylcarbamate (moles of peroxide) | .015 | — |
| 1,3-Dimethyl-3-(t-butylperoxy)butyl alcohol (moles of peroxide) | — | .015 |
| Cure temp. °F/time | 320° F for 30 min. | |
| Shore hardness | 55 | 55 |
| % Compression set | 10 | 14 |
| 300% Modulus, psi | 1485 | 1020 |
| Ultimate tensile, psi | 2135 | 2140 |
| % Elongation | 400 | 595 |
| Cure temp. °F/time | 320° F for 45 min. | |
| Shore hardness | 55 | 54 |
| % Compression set | 9 | 11 |
| 300% Modulus, psi | 1540 | 1155 |
| Ultimate tensile, psi | 2155 | 2265 |
| % Elongation | 400 | 560 |

In comparative Table I the EPR polymeric compound formulations were an ethylene-propylene rubber, EPR404, sold by Enjay Chemical Company and had about a 43:57 ethylene:propylene content, a specific gravity of 0.86, a Mooney Viscosity, 8ML/212° F of 40, and an ash content of 0.2 weight percent. No oil extender was present in these formulations. A carbon black reinforcing material (Semi Reinforcing Furnace black-SRF) was present and sulfur was used as a coagent. The only difference in the formulations of the invention and the prior art was in the liquid peroxy crosslinking agent, the novel peroxy carbamate compound of the invention versus the peroxy alcohol of the prior art. In these formulations no carrier was present.

Crosslinking efficiency is measured by a high Modulus, a low elongation and a low compression set. The two cures in Table I clearly show that formulation of the invention, in equimolar concentration in EPR with the prior art's formulation, gives better crosslinking than the prior art because in both cures the compression set and elongation were significantly lower than the prior art's and the Modulus significantly higher. These comparative tests show that formulation of the invention using the novel peroxy carbamate compound cured to a greater crosslinking density than the peroxy alcohol of the prior art.

TABLE II

Crosslinking of Polyethylene (DYNH-1-100 PHR)

Peroxide
1,3-Dimethyl-3-(t-butylperoxy)butyl n-butyl carbonate (C-I)
1,3-Dimethyl-3-(t-butylperoxy)butyl N-methylcarbamate (C-III)
1,3-Dimethyl-3-(t-butylperoxy)butyl N,N-dimethylcarbamate (C-IV)
1,3-Dimethyl-3-(t-butylperoxy)butyl alcohol (R-2)

| | moles (equivalents of peroxide) | | | | | | |
|---|---|---|---|---|---|---|---|
| C-I | — | — | 0.01 | 0.013 | — | — | — |
| C-III | 0.01 | 0.015 | — | — | — | — | — |
| C-IV | — | — | — | — | 0.015 | — | — |
| R-2 | — | — | — | — | — | 0.01 | 0.015 |
| Cure Temperature | | | | 320° F for 30 min. | | | |
| %Crosslinking | *84.8 | 86.6 | 83.3 | 84.9 | 81.7 | 75.2 | 79.6 |
| Cure Temperature | | | | 340° F for 30 mmin. | | | |
| %Crosslinking | 85.5 | 89.1 | 87.6 | 89.0 | 84.6 | 74.4 | 78.8 |
| Cure Temperature | | | | 375° F for 30 min. | | | |
| %Crosslinking | 85.1 | 88.2 | 87.1 | 89.0 | 84.4 | 69.2 | 76.1 |

*By solvent Extraction in Xylene at 80° C for 24 hours.

The polyethylene used in the examples of TABLE II was a commercial low density polymer with 0.918 density of 2.0 melt index. (DYNH-1 Bakelite Polyethylene-marketed by Union Carbide Corp.)

TABLE II shows at equimolar concentrations of the peroxy compounds in the polyethylene formulations that the C-III peroxy carbamate compound formulation is about as efficient as the C-I peroxy carbonate formulation and significantly more efficient than the R-2 peroxy alcohol compound formulation as a crosslinking agent. The C-IV peroxy carbamate compound formulation is also more efficient than the R-2 formulation.

TABLE III

Crosslinking Polyurethane Rubber

| Formulation | | | | |
|---|---|---|---|---|
| Genthane S | 100 parts | | | |
| High Abrasion Furnace (HAF)Carbon black | 25 PHR | | | |
| Stearic acid | 0.2 PHR | | | |
| Peroxide | moles (equivalent of peroxide) | | | |
| C-III | 0.010 | 0.015 | — | — |
| R-2 | — | — | 0.010 | 0.015 |
| Cure Temperature | 320° F for 30 min. | | | |
| Shore hardness | 62 | 67 | 55 | 53 |
| % Compression Set | 11 | 5 | 30 | 17.5 |
| 300% Modulus | 2165 | 3690 | 880 | 1138 |
| Ultimate Tensile | 5665 | 3690 | 4820 | 4287 |
| % Elongation | 500 | 240 | 710 | 617 |
| Cure Temperature | 320° F for 45 min. | | | |
| Shore hardness | 62 | 66 | 55 | — |
| % Compression Set | 8 | 6 | 30 | — |
| 300% Modulus | 2220 | 3990 | 845 | — |
| Ultimate Tensile | 5190 | 4503 | 4385 | — |
| % Elongation | 490 | 333 | 775 | — |

The polyurethane rubber, used in the formulations of TABLE III, was a commercial product of the General Tire and Rubber Company marketed as Genthane ®-S with a Specific Gravity of 1.19 and a Mooney Viscosity (ML-4 at 212° F) of 50±10. This material contained 0.2 PHR stearic acid which was added as a lubricant.

Again the comparative TABLE III demonstrates the superior crosslinking efficiency of the formulation of the invention using a novel compound over the prior are peroxy alcohol formulation. This superior crosslinking is shown by the much lower compression set and elongation and the much higher Modulus.

CURING POLYESTER RESIN BLEND

Two compounds, C-II and C-V, were used as curing agents for a styrene-polyester resin blend in the amount of 1% by weight of agent per 100 parts by weight of blend. The blend was prepared by mixing 7 parts by weight of resin and 3 parts by weight of styrene monomer. The resin was the polycondensate of 1.0 mole of maleic anhydride, 1.0 mole of phthalic anhydride and 2.2 moles of propylene glyol; the polyester resin had an acid No. of 45–50.

The S.P.I. gel times, cure times and exotherms were determined (S.P.I.) procedure for running exotherm curves — polyester resins, *Modern Plastics*, 39, pp. 147 ff. August 1962.) These tests were run at 100° C. The results are set out below.

| Compounds | C-II | C-V |
|---|---|---|
| Gel Time, min. | 4.5 | 15.7 |
| Cure Time, min. | 6.2 | 28.2 |
| Peak Exotherm, F. | 420 | 318 |

The above data indicates that C-II is a medium temperature peroxide initiator or curing agent while C-V is a higher temperature initiator.

The above working examples are illustrative only and do not limit the scope of the invention, which is as set forth in the description herein. However, these working examples establish that the defined peroxy compounds are safe, efficient and outstandingly effective vulcanizing agents.

Thus having described the invention what is claimed is:

1. A peroxy compound of the formula:

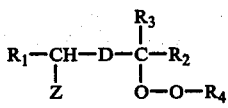

where:
(a) $R_1$ is hydrogen or an alkyl of 1–4 carbons;
(b) $R_2$ and $R_3$ are an alkyl of 1–4 carbons;
(c) $R_4$ is t-alkyl of 4–8 carbons;
(d) Z is

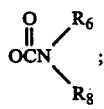

(e) $R_6$ and $R_8$ are independently H, alkyl of 1–8 carbons;
(f) D is ethynyl diradical diethynyl diradical or alkyl diradical having 1–8 carbons.

2. 1,3-Dimethyl-3-(t-butylperoxy)butyl N,N-dimethyl carbamate.

3. 1,3-Dimethyl-3-(t-butylperoxy)butyl N-methyl carbamate.

4. In a vulcanizable composition comprising an intimate mixture of a polymeric compound capable of being crosslinked to form a thermoset material and a crosslinking agent in an amount sufficient to afford the desired degree of crosslinking, the improvement comprising using as said agent a peroxy compound of the formula:

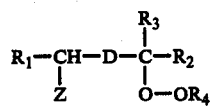

where:
(a) $R_1$ is hydrogen or an alkyl of 1–4 carbons;
(b) $R_2$ and $R_3$ are an alkyl of 1–4 carbons;
(c) $R_4$ is t-alkyl of 4–8 carbons;
(d) Z is

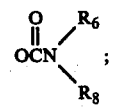

(e) $R_6$ and $R_8$ are independently H, alkyl of 1–8 carbons;
(f) D is ethynyl diradical or alkyl diethynyl diradical having 1–8 carbons.

5. The composition of claim 4 wherein the polymeric compound is selected from the group consisting of polyethylene, ethylene-propylene rubber, nitrile rubber, natural rubber, silicone rubber, polyurethane rubber, polyester resin, and ethylene-vinyl acetate copolymer.

6. The composition of claim 5 wherein a filter is present.

7. A vulcanizable composition which comprises an intimate mixture of ethylene-propylene rubber and 1–5 PHR of 1,3-dimethyl-3-(t-butylperoxy)butyl N-methyl-carbamate.

8. A method of making a crosslinked material which comprises heat curing the vulcanizable composition of claim 4 for a time sufficient to obtain the desired degree of crosslinking.

* * * * *